Figure 1:
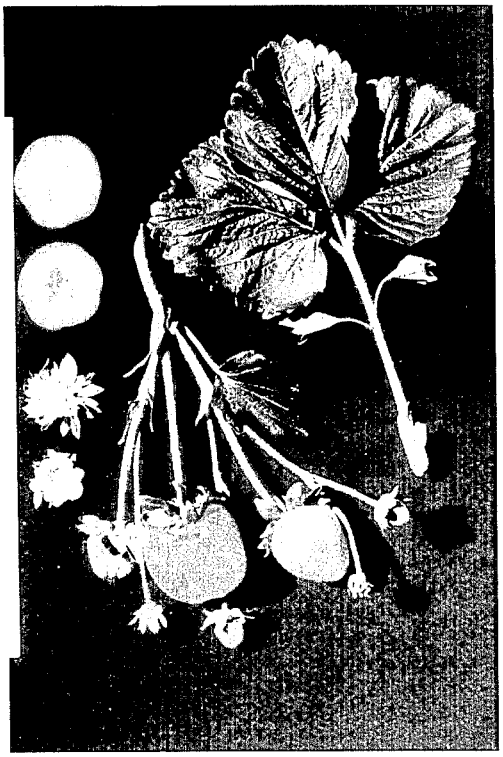

United States Patent [19]

Johnson, Jr. et al.

[11] Patent Number: Plant 6,191

[45] Date of Patent: May 31, 1988

[54] STRAWBERRY PLANT NAMED 'SWEDE'

[75] Inventors: Harold A. Johnson, Jr.; Amado Q. Amorao; Joseph I. Espejo, Jr., all of Watsonville, Calif.

[73] Assignee: Driscoll Strawberry Associates Inc., Watsonville, Calif.

[21] Appl. No.: 862,347

[22] Filed: May 12, 1986

[51] Int. Cl.[4] ..... A01H 5/03

[52] U.S. Cl. ..... Plt./48

[58] Field of Search ..... Plt./48

*Primary Examiner*—Robert E. Bagwill

*Attorney, Agent, or Firm*—Townsend and Townsend

[57] ABSTRACT

A new and distinct spring bearing variety of strawberry plant, characterized by its ability to produce an early large crown crop, even in central California, with large fruit size. It has the ability to produce from April to October with a minimum of runners if transplants are given the correct chilling, at both the nursery and cold storage, before being planted.

The variety is particularly distinguished by its good fruit appearance and flavor, and its dark small to medium sized plant. The fruit are produced close to the plant, but located so that they are easily available to pickers, making the variety desirable to the pickers.

1 Drawing Sheet

This invention relates to a new and distinct spring bearing variety of strawberry plant known as 'Swede,' which is a result of a cross of two Driscoll Strawberry Associates, Inc. non-patented selections D5.23 and B6.117.

The seedlings resulting from the aforementioned cross were grown and asexually multiplied in Shasta County, Calif., and tested in the fruiting beds on the property of growers of the Driscoll Strawberry Associates, Inc. Clones of the seedlings were also held at the Propagation Nursery in Shasta County. One plant was selected from the aforementioned group of seedlings and further asexually reproduced in the Shasta County nursery of Driscoll Strawberry Associates, Inc. Tests followed in various parts of California during intervening seasons on various properties of grower members of the Driscoll Strawberry Associates, Inc. These tests indicated the merits of 'Swede' and resulted in its selection as a promising test variety.

In the drawing, FIG. 1 is a photograph of plant parts of the new variety, typical in size, shape, and color. The berry in cross section illustrates flesh color and characteristic core cavity. The inflorescence pictured illustrates typical branching and relative size about the middle of June. Long strong pedicels are present even on those holding secondary and tertiary berries. The drawing shows hair on these pedicels that are abundant and are directed perpendicular to the pedicels. The flowers show overlapping petals and a calyx with anthers producing an abundance of pollen. The ripe primary berry is typical wedge shaped with some longitudinal ribbing, but many subsequent primaries are more conic, and are similar to the ripening secondary berry present giving a more conic appearance. The leaf present is typical of the dark color found on this new variety, and the rugose development of the leaflets and the bracts on the petiole.

The novel plant of 'Swede' is small to medium in size, but vigorous if it is planted with adequate chilling before being planted. Its crown crop is considered outstanding for the central coast region in that this crop is early, having large berries with excellent appearance. These berries are borne on thick long pedicels, and have a showy gloss making them attractive enough to be picked for the "Long Stem" market. To make a grade of what Driscoll considers "Long Stem" grade, there can't be more than 120 berries per crate. Because of the abundant crown crop (the crop that is initiated at the nursery before being dug), it is important that the young plant supporting this crop be as strong as possible. If the chilling isn't adequate before being planted, or essential nutrients are not available after being planted, the stress on the plant may cause limited plant growth for the remainder of the production year. The main crop also comes early for the central coast region. The remaining summer and fall crops come early and are of high quality, but limited in total production. The number of berries per plant remains small as tertiary berries often do not develop. This contributes to consistently good fruit size. Even though there are typical cycles in production, there is consistent availability of fruit for pickers throughout the season. Primary berries of the main crop tend to develop wedge shape with slight ribbing, but secondary berries as well as subsequent primaries tend to be more conic and symmetrical. The flowers and subsequent fruit of all crops are borne close to the crown, reflecting a short inflorescence and pickers consider the fruit from this variety easy to pick. The foliage of this new variety is noticeably dark during the entire season.

The plant of this invention is distinguished from other varieties by its flowers, fruit, and plant characteristics. There are periods when the flower of 'Swede' is visible above the plant, but the bloom is mostly within the leaf canopy in contrast to 'Heidi.' 'Heidi' produces an abundance of visible flower above the plant. While 'Swede' is capable of continuous production from an early March and April crown crop to fall production, it is influenced negatively by excessive chilling or environmental conditions that prevent its ability to initiate a late summer crop in contrast to 'Heidi.' The crop may be detrimentally influenced by too much chilling, but excessive amounts of runners are not produced, even less than 'Heidi' if given the same chilling. 'Heidi's' fall production is not as easily influenced by environmental factors. Even though the flower pistils are large and anthers develop on short stamens, the anthers are large and seem to produce adequate pollen to allow for complete fertilization even early in the season. Unfertilized seed at the apex of ripening fruit is rare as compared to 'Heidi,' U.S. Plant Pat. No. 3,123. 'Heidi' is prone to produce fruit with white tips as a result of unfertilized seed. The fruit is also larger than 'Heidi,' coming from pedicels that are thicker and stronger than those of 'Heidi.' This is especially true of the crown crop and crops after the main crop. The fruit is generally darker than 'Heidi' if picked at the same stage of maturity. The new variety produces fewer berries per inflorescence and fewer inflorescence per plant than 'Heidi,' but 'Swede' produces large berries with very few berries small enough to be discarded. Pedicels of 'Swede' are thicker and stronger than those of 'Heidi,' and the hair on pedicels is mostly perpendicular to the pedicel in contrast to 'Heidi' whose hair is mostly parallel to the pedicel.

The plant of 'Swede' is smaller, but more dense than 'Heidi,' its leaves are darker, its leaflets are thicker, and its serrations are less pointed than 'Heidi.' The petiolule of 'Swede' is greater in length than that of 'Heidi.' The inflorescence of 'Swede' is shorter than 'Heidi' with most of its fruit ripening close to the plant crown in contrast to 'Heidi' where berries often ripen on the shoulders of the beds or in the ditch. The pubescence on 'Swede's' foliage is more abundant than on the foliage of 'Heidi.' The crown crop of 'Swede' is earlier, larger, and with larger fruit size than that of 'Heidi.' The main crop is also earlier with primaries equal in size, but secondaries and tertiaries are larger on 'Swede.' The fruit of 'Swede' is susceptible to rain damage and Botrytis, but not as susceptible as 'Heidi.' The berry shapes of 'Heidi' and 'Swede' are similar, but 'Swede' tends to be more globular during the main crop in July, and doesn't have the white tips that show in a percentage of the 'Heidi.' Both varieties show field susceptibility of Verticillium wilt, and vascular collapse due mainly to *Phytophthora cactorum.* As a seedling and selection, this variety withstood the natural invasion of certain virus components found in central California without losing its ability to produce.

The varietal characteristics described below in detail were observed during the first fruiting season after a November planting. The plants had been dug at a California high elevation nursery three to five weeks before the planting date. Observations were made in Watsonville and Santa Maria which are cool coastal areas near the Pacific Ocean. The color terminology is in accordance with the Munsell Color System.

*Plants.*—Small to medium and vigorous if given ample chilling before being planted.

*Leaves.*—Medium to large in size. Central leaflet is usually 6 to 9 cm with the length averaging slightly greater than the width. Petiolules average 17 mm in length. Bracts are generally present on petioles. Leaflet serrations are abundant, but considered only moderately deep with a moderately acute apex. The color of the upper side of leaflet is 8.9 GY-2.3/4.7.

*Runners.*—Runners are vigorous, but only medium in abundance both at the nursery and in the fruiting bed.

*Inflorescence.*—Mostly short in total length, but some may reach 20 to 30 cm. Peduncles are short and thick. Pedicels are thick, but not considered short. Secondary and tertiary berries are borne on pedicels that extend past the primary berry and there are relatively few tertiary berries present. The pedicel holding the primary berry originates mainly at the axil of secondary peduncles. Hair on tertiary pedicels 20 mm from the fruit is perpendicular to the pedicel. Some flowers may be visible above the plant, and flowers are large in diameter, 30 or more mm in diameter. Anthers produce an abundance of pollen even during the early spring.

*Fruit.*—Berries from the crown crop are large, nearly equal to those of the main crop. Primaries of main crop are 40 to 50 mm in length with the width often greater than the length. Surface mainly smooth except for the main crop primaries that show some longitudinal ribbing. Surface has high gloss if not over-ripe. Fruit shape is mainly conic to globose-conic except for primaries of the main crop and some crown crop berries that are short wedge to medium wedge as pictured in the USDA Bulletin 1043. Shoulders are rounded, not necked. Seeds are small to medium in size, remaining yellow in color, except if overexposed to full sun. Unfertilized seed at apex of fruit is uncommon. Surface color 5.5 R-2.9/11.6, and flesh near surface 6.2 R-4.0/16.3.

*Calyx.*—Large in diameter with primaries during June becoming 45 to 50 mm in diameter. Considerable overlap to sepals. Serrations on sepals may be present on primaries, not abundant on secondaries. Color of sepals on side facing fruit is 8.9 GY-2.3/4.0.

We claim:

1. The new and distinct variety of strawberry plant herein described and illustrated, and identified by the characteristics enumerated above.

* * * * *